United States Patent [19]

Lavielle et al.

[11] Patent Number: 5,703,070
[45] Date of Patent: Dec. 30, 1997

[54] INDOLE, INDAZOLE AND BENZISOXAZOLE COMPOUNDS

[75] Inventors: Gilbert Lavielle, La Celle Saint Cloud; Olivier Muller, Ennery; Mark Millan, Paris; Valérie Audinot, Croissy, all of France

[73] Assignee: Adir et Compagnie, Courbevoie, France

[21] Appl. No.: 663,464

[22] Filed: Jun. 6, 1996

[30] Foreign Application Priority Data

Jun. 7, 1995 [FR] France .................. 95 06663

[51] Int. Cl.$^6$ .............. C07D 209/04; C07D 231/56; A61K 31/40; A61K 31/41
[52] U.S. Cl. .............. 514/212; 514/373; 514/379; 514/406; 514/419; 540/602; 540/603; 548/207; 548/241; 548/361.1; 548/362.5; 548/468
[58] Field of Search ............... 548/207, 241, 548/361.1, 362.5, 468; 540/602, 603; 514/212, 373, 379, 406, 419

[56] References Cited

U.S. PATENT DOCUMENTS

| | | | |
|---|---|---|---|
| 5,030,639 | 7/1991 | Davis | 514/322 |
| 5,077,288 | 12/1991 | Lavielle et al. | 514/210 |
| 5,134,147 | 7/1992 | Peglion et al. | 514/300 |
| 5,145,845 | 9/1992 | Johnson et al. | 514/80 |
| 5,348,968 | 9/1994 | Lavielle et al. | 514/360 |
| 5,500,443 | 3/1996 | Lavielle et al. | 514/422 |

Primary Examiner—Mukund J. Shah
Assistant Examiner—Deepak R. Rao
Attorney, Agent, or Firm—The Firm of Gordon W. Hueschen

[57] ABSTRACT

Compound of formula (I):

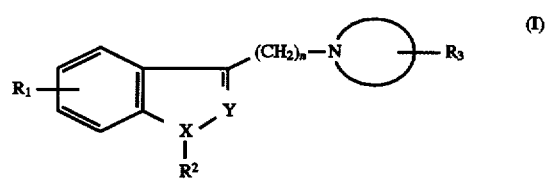

in which:

$R_1$ represents hydrogen, halogen, alkyl, alkoxy, trihalomethyl or hydroxyl, $R_2$ represents hydrogen, alkyl or phenyl which is optionally substituted,

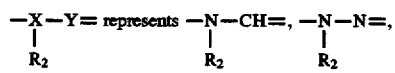

or alternatively

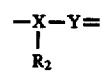

represents —O—N=, $1 \leq n \leq 6$,

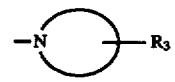

represents any one of the groups defined in the description, its isomers and its addition salts with a pharmaceutically acceptable acid or base, a medicinal products containing the same are useful in the treatment of schizophrenia.

9 Claims, No Drawings

INDOLE, INDAZOLE AND BENZISOXAZOLE COMPOUNDS

BACKGROUND OF THE INVENTION

The present invention relates to new indole, indazole and benzisoxazole compounds.

1. Field of the Invention

Numerous indole derivatives have been described in the literature. Some of them have been developed as agonists of 5-HT$_{1-like}$ receptors in the treatment and the prevention of pains caused by an abnormal vascular flow, such as migraine and associated diseases. This is more particularly the case with the compounds described in Patents EP 382,570, DE 3,131,728, EP 438,230 and EP 486,666. Patent DE 2,708,913 describes indole derivatives having sedative, analgesic and hypotensive properties. Patent EP 135,781 describes, for its part, indazole derivatives as central analgesics having neuroleptic properties. Finally, Patent EP 518,805 describes indole, indazole and benzisoxazole derivatives which are powerful ligands for sigma receptors.

The compounds of the present invention, as well as being novel, have particularly advantageous pharmacological properties. Indeed, one of the challenges of psychopharmacology today is to find new medicaments which allow better control of schizophrenia, the treatment of which is currently rather unsatisfactory. Conventional neuroleptics, such as haloperidol, treat productive symptoms (such as fantasizing and hallucinations) fairly well but their effectiveness with respect to deficiency symptoms (such as social withdrawal) is very low. Moreover, they cause an extrapyramidal syndrome of Parkinsonian type, as has been shown by A. Y. Deutch et at. (Schizophrenia Research, 4, 121–151, 1991) and H. Y. Meltzer et at. (Pharmacol. Rev., 43, 587–604, 1991).

Unlike haloperidol, clozapine is more effective in treating deficiency symptoms and is even effective in patients who resist haloperidol. Moreover, it causes virtually no extrapyramidal syndrome, as has been shown by Coward et al. (Psychopharmacology, 99, s6–s12, 1989). This difference seems to be due to the receptor profile of clozapine, which is different from that of haloperidol: for example, its low relative activity with respect to D$_2$ receptors and its relatively strong affinity with respect to serotoninergic receptors, more particularly 5-HT$_{2A}$ and 5-HT$_{2C}$ receptors. These results have been shown by H. Canton et at. (Eur. J. Pharmacol., 191, 93–96, 1990) and by A. Y. Deutch and H. Y. Meltzer, cited above.

Moreover, as regards its absence of cataleptogenic effect, unlike haloperidol, clozapine shows a degree of affinity for 5-HT$_{1A}$ receptors, the activation of which is moreover associated with anxiolytic, antidepressant and, optionally even, antipsychotic effects, as has been shown by S. Ahlenius (Pharmacol. & Toxicol., 64, 3–5, 1989), J. E. Barrett et at. (in "5-HT$_1$A agonists, 5-HT$_3$ antagonists and benzodiazepines: their comparative behavioural pharmacology", edited by R. J. Rogers and S. I. Cooper, Wiley & Sons Ltd., Chichester, p. 59–105, 1991), M. J. Millan et al. (Drug News Perspectives, 5, 397–466, 1992) and J. M. A. Sitsen (Drug News & Perspectives, 4, 414–418, 1991).

Nevertheless, due to its toxicity, clozapine cannot be envisaged in the general treatment of schizophrenic conditions. It was therefore particularly advantageous to find products sharing the mechanism of the latter but which lack its toxic effects, which are directly related to its specific chemical structure.

The compounds described in this patent correspond to the desired profile. Indeed, they exhibit (in vitro and in vivo) a biochemical and functional profile very similar to that of clozapine and with, moreover, greater affinities for 5-HT$_{1A}$, 5-HT$_{2A}$ and/or 5-HT$_{2C}$ receptors. They thus possess a novel profile which seems to be well suited to a better treatment of schizophrenia in comparison with that which it is currently possible to obtain with the available products.

2. Prior Art Description

Moreover, this entirely remarkable pharmacological profile has not been obtained with the closest compounds of the prior art which possess, in their structure, a piperidine ring in place of a pyrrolidine or perhydroazepine ring, as is the case with the derivatives of the present invention.

DETAILED DESCRIPTION OF THE INVENTION

More specifically, the present invention relates to compounds of formula (I):

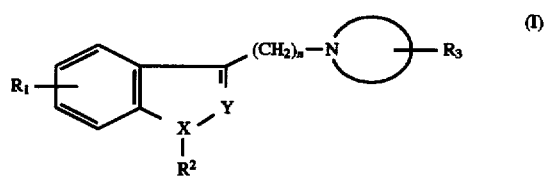

in which:

R$_1$ represents a hydrogen or halogen atom or a linear or branched (C$_1$–C$_6$)alkyl, linear or branched (C$_1$–C$_6$) alkoxy, trihalomethyl or hydroxyl group, R$_2$ represents a hydrogen atom or a linear or branched (C$_1$–C$_6$)alkyl or phenyl group (which is unsubstituted or substituted by one or a number of halogen atoms or alkyl, alkoxy, hydroxyl or trihalomethyl group),

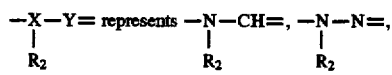

or alternatively

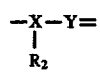

represents —O—N=, 1≦n≦6

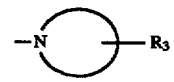

represents any one of the following groups:

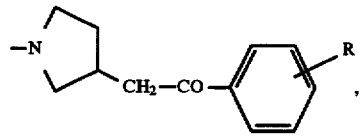

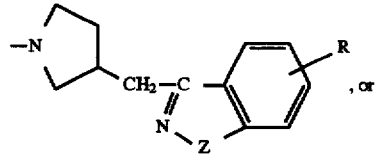

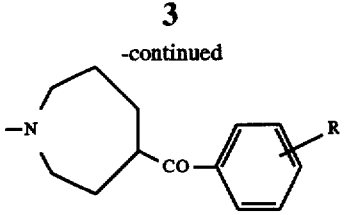

in which:

R represents a hydrogen or halogen atom or a linear or branched ($C_1$–$C_6$)alkyl, linear or branched ($C_1$–$C_6$) alkoxy, hydroxyl or trihalomethyl group, Z represents an oxygen or sulfur atom or an —NH— group, to their isomers and to their addition salts with a pharmaceutically acceptable acid or base.

Isomer is understood to mean enantiomers, diastereoisomers and epimers, as well as conformational isomers.

Mention may be made, among pharmaceutically acceptable acids, without implied limitation, of hydrochloric, hydrobromic, sulfuric, phosphonic, acetic, trifluoroacetic, lactic, pyruvic, malonic, succinic, glutaric, fumaric, tartaric, maleic, citric, ascorbic, oxalic, methanesulfonic and camphoric acids and the like.

Mention may be made, among pharmaceutically acceptable bases, without implied limitation, of sodium hydroxide, potassium hydroxide, triethylamine, tert-butylamine, and the like.

The invention also applies to the process for the preparation of the compounds of formula (I), which comprises the use, as starting material, of an alcohol of formula (II):

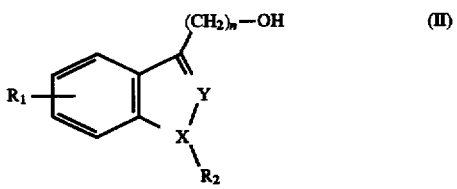

in which $R_1$, $R_2$, X, Y and n have the same meaning as in the formula (I), which is converted to the corresponding brominated derivative using carbon tetrabromide in the presence of triphenylphosphine, in order to result in the compound of formula (III):

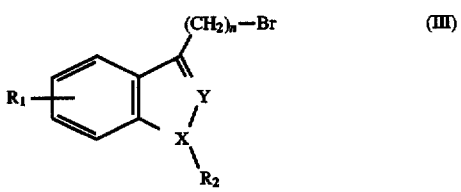

in which $R_1$, $R_2$, X, Y and n have the same meaning as in the formula (I), which is reacted with an amine of formula (IV):

in which $R_3$ has the same meaning as in the formula (I), in order to result in the compound of formula (I), which:
- can be, if appropriate, purified according to a conventional purification technique,
- is separated, if appropriate, into its isomers according to a conventional separation technique,
- is converted, if desired, into its addition salts with a pharmaceutically acceptable base.

The compounds of formula (II) are obtained:
- when n is equal to 1, by reduction of the corresponding acids or aldehydes by lithium aluminum hydride;
- when n is equal to 2 or 3, by reaction of a correctly substituted phenylhydrazine with 2-ethoxytetrahydrofuran (n=2) or 2-methoxytetrahydropyran (n=3), according to the method described in Patent BE 892,145;
- when n>3, by conversion of the brominated derivatives of formula (III) to the corresponding nitriles, then by alcoholysis to the corresponding esters and then reduction to the alcohol and so on until the desired chain length is obtained.

The compounds of formula (II) in which

are more specifically obtained according to the process described in Patent JP 8031050.

The compounds of formula (IV), such that

represents the group:

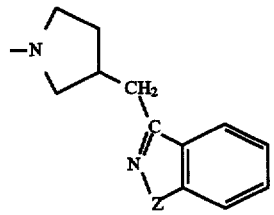

are obtained according to the process described in Patent EP 061,034.

Another subject of the present invention is the pharmaceutical compositions containing, as active principle, at least one compound of formula (I), alone or in combination with one or a number of nontoxic inert excipients or vehicles.

Mention may more particularly be made, among the pharmaceutical compositions according to the invention, of those which are suitable for oral, parenteral or nasal administration, simple or sugar-coated tablets, sublingual tablets, gelatin capsules, lozenges, suppositories, creams, ointments, dermal gels, and the like.

The useful dose varies according to the age and the weight of the patient, the nature and the severity of the complaint and the administration pathway. The latter may be oral, nasal, rectal or parenteral. Generally, the unit dose varies between 10 µg and 100 mg for a treatment taken 1 to 3 times per 24 hours.

The following Examples illustrate the invention and do not limit it in any way. The starting materials used are known products or products prepared according to known procedures.

EXAMPLE 1

3-{2-[3-(4-Fluorobenzoylmethyl)pyrrolidin-1-yl]ethyl}-5-methoxyindole hydrochloride Stage 1

2-(5-Methoxyindol-3-yl)ethanol

A solution of 15 g of (5-methoxyindol-3-yl)acetic acid (0.073 mol) in 100 ml of tetrahydrofuran is added to a suspension of 2.1 g (0.219 mol) of lithium aluminum hydride in 100 ml of ethyl ether and the reaction mixture is brought to reflux for 6 hours. The reaction mixture is then hydrolyzed with 80 ml of a saturated aqueous magnesium sulfate solution. The whole mixture is filtered through celite and the solvents are evaporated under vacuum. The residue is taken up in a small amount of water and extracted a number of times with dichloromethane. The product is obtained after evaporation of the solvant.

Stage 2
3-(2-Bromoethyl)-5-methoxyindole

A mixture of 10 g of the product obtained in Stage 1 (0.0523 mol), 16.5 g of triphenylphosphine (0.0628 mol), 17.3 g of carbon tetrabromide (0.0628 mol) and 200 ml of acetonitrile is left stirring for 2 hours. The solvent is then evaporated under vacuum and the product purified by chromatography on a silica column, Merck 70–230 mesh, using dichloromethane as eluent.

Stage 3
3-{2-[3-(4-Fluorobenzoylmethyl)pyrrolidin-1-yl]ethyl}-5-methoxyindole

A mixture of 5 g (0.0197 mol) of the product obtained in Stage 2, 4 g (0.0216 mol) of 3-(4-fluorobenzoylmethyl) pyrrolidine, 0.1 g of sodium iodide and 3 g of potassium carbonate in 100 ml of diethyl ketone is brought to reflux for 24 hours. The inorganic salts are then filtered off, the solvent is evaporated under vacuum, the residue is taken up in 100 ml of dichloromethane and this organic phase is washed with 100 ml of water. After drying over magnesium sulfate and evaporation of the solvent, the residue is purified by chromatography on a silica column, Merck 70–230 mesh, using a dichloromethane/methanol/aqueous ammonia (97/3/0.3) mix-ture as eluent.

Stage 4
3-{2-[3-(4-Fluorobenzoylmethyl)pyrrolidin-1-yl]ethyl}-5-methoxyindole hydrochloride One equivalent of hydrogen chloride in solution in ethanol is added to an acetone solution of the product obtained in Stage 3. Complete evaporation of the solvents results in the hydrochloride of the compound mentioned.

Elemental microanalysis:

|  | C % | H % | N % | Cl % |
|---|---|---|---|---|
| Calculated | 66.26 | 6.29 | 6.72 | 8.50 |
| Found | 66.53 | 6.30 | 6.38 | 8.13 |

EXAMPLE 2

1-Methyl-3-{2-[3-(4-fluorobenzoylmethyl) pyrrolidin-1-yl]ethyl}-5-methoxyindole hydrochloride Stage 1
Methyl 2-(5-methoxy-1-methylindol-3-yl)acetate 8.2 g (0.1464 mol) of powdered potassium hydroxide and 13.8 g (0.0972 mol) of methyl iodide are added to a solution of 10 g (0.0487 mol) of (5-methoxyindol-3-yl)acetic acid in 120 ml of acetone. After stirring for 4 hours at room temperature, 13.8 g of methyl iodide are again added and then, 12 hours later, 13.8 g of methyl iodide and 8 g of potassium hydroxide are again added. The whole reaction mixture is then concentrated, the residue is taken up in water and extracted with dichloromethane, the organic phase is washed with a 1N sodium hydroxide solution and then with 1N hydrochloric acid and separated by settling, the organic solution is dried over magnesium sulfate and the solvent evaporated under vacuum.

Stage 2
2-(5-Methoxy-1-methylindol-3-yl) ethanol

Reduction of the ester obtained in Stage 1 is carded out according to the procedure described in Stage 1 of Example 1.

Stage 3
3-(2-Bromoethyl)-5-methoxy-1-methylindole

Bromination of the alcohol obtained in Stage 2 is carried out in the same way as that described in Stage 2 of Example 1.

Elemental microanalysis:

|  | C % | H % | N % | Br % |
|---|---|---|---|---|
| Calculated | 53.75 | 5.26 | 5.22 | 29.8 |
| Found | 53.60 | 5.21 | 5.20 | 29.7 |

Stage 4
1-Methyl-3-{2-[3-(4-fluorobenzoylmethyl)pyrrolidin-1-yl] ethyl}-5-methoxyindole Alkylation of 3-(4-fluorobenzoylmethyl)pyrrolidine by the brominated compound obtained in Stage 3 is carded out in diethyl ketone by following the procedure described in Stage 3 of Example 1.

Stage 5
1-Methyl-3-{2-[3-(4-fluorobenzoylmethyl)pyrrolidin-1-yl] ethyl}-5-methoxyindole hydrochloride Salification of the compound obtained in Stage 4 of Example 2 is carded out in a way similar to that described in Stage 4 of Example 1.

Elemental microanalysis:

|  | C % | H % | N % | Cl % |
|---|---|---|---|---|
| Calculated | 66.89 | 6.55 | 6.50 | 8.24 |
| Found | 65.22 | 6.43 | 6.29 | 8.15 |

EXAMPLE 3

3-{3-[3-(4- Fluorobenzoylmethyl)pyrrolidin-1-yl] propyl}-5-methoxyindole hydrochloride Stage 1
3-(5-Methoxyindol-3-yl)propan-1-ol This alcohol is synthesized according to the method described in Belgian Patent BE 892,145, 4-methoxyphenylhydrazine hydrochloride and 2-methoxytetrahydropyran being used as starting materials.

Stage 2
3-(3-Bromopropyl)-5-methoxyindole

This compound is synthesized according to the method described in Stage 2 of Example 1, the compound of Stage 1 of Example 3 being used as starting material.

Stage 3
3-{3-[3-(4-Fluorobenzoylmethyl)pyrrolidin-1-yl]propyl}-5-methoxyindole

This compound is synthesized according to the method described in Stage 3 of Example 1, from the compound described in the preceding stage.

Stage 4
3-{3-[3-(4-Fluorobenzoylmethyl)pyrrolidin-1-yl]propyl}-5-methoxyindole hydrochloride Salification is carded out in the same way as that described in Stage 4 of Example 1.

Elemental microanalysis:

|  | C % | H % | N % | Cl % |
|---|---|---|---|---|
| Calculated | 66.89 | 6.55 | 6.50 | 8.23 |
| Found | 66.53 | 6.47 | 6.24 | 8.00 |

EXAMPLES 4 AND 5

α and β isomers of 3-{3-[3-(4-fluorobenzoylmethyl)pyrrolidin-1-yl]propyl}-5-methoxyindole hydrochloride Synthesis of the enantiomers of the compound of Example 3 (racemic) is carried out by using the pure enantiomers of 3-(4-fluorobenzoylmethyl)pyrrolidine, the preparation of which has been described in Patent EP 389,352.

Yield: 45%

EXAMPLE 4

α isomer

Elemental microanalysis:

|  | C % | H % | N % | Cl % |
|---|---|---|---|---|
| Calculated | 66.89 | 6.55 | 6.50 | 8.23 |
| Found | 67.00 | 6.56 | 6.07 | 8.27 |

Optical rotation: $[\alpha]_D^{21}=1.85°$ (c=1%, DMSO)
Enantiomeric purity: ≧99% (chiral column)

EXAMPLE 5

β isomer

Elemental microanalysis:

|  | C % | H % | N % | Cl % |
|---|---|---|---|---|
| Calculated | 66.89 | 6.55 | 6.50 | 8.23 |
| Found | 66.90 | 6.55 | 6.65 | 8.19 |

Optical rotation: $[\alpha]_D^{21}=+1.40°$ (c=1%, DMSO)
Enantiomeric purity: ≧99% (chiral column)

EXAMPLE 6

1-Methyl-3-[3-[3-(4-fluorobenzoylmethyl)pyrrolidin-1-yl]propyl]-5-methoxyindole hydrochloride Stage 1
3-(5-Methoxy-1-methylindol-3-yl)propan-1-ol The expected product is obtained by methylation of the 3-(5-methoxyindol-3-yl)propan-1-ol described in Stage 1 of Example 3 by using the technique described in Stage 1 of Example 2.

Elemental microanalysis:

|  | C % | H % | N % |
|---|---|---|---|
| Calculated | 71.21 | 7.81 | 6.39 |
| Found | 71.37 | 7.56 | 6.20 |

Stage 2
3-(3-Bromopropyl)-5-methoxy-1-methylindole

Synthesis of the brominated derivative is carried out according to the method described in Stage 2 of Example 1.

Stage 3
1-Methyl-3-{3-[3-(4-fluorobenzoylmethyl)pyrrolidin-1-yl]propyl}-5-methoxyindole Alkylation of 3-(4-fluorobenzoylmethyl)pyrrolidine by the brominated derivative obtained in the preceding stage is carded out according to the procedure described in Stage 4 of Example 2.

Stage 4
1-Methyl-3-{3-[3-(4-fluorobenzoylmethyl)pyrrolidin-1-yl]propyl}-5-methoxyindole hydrochloride Salification is carried out with an ethanolic solution of hydrogen chloride on the compound obtained in Stage 3 dissolved in acetone.

Elemental microanalysis:

|  | C % | H % | N % | Cl % |
|---|---|---|---|---|
| Calculated | 67.48 | 6.80 | 6.30 | 7.97 |
| Found | 67.24 | 6.70 | 6.24 | 8.09 |

EXAMPLE 7

3-{3-[4-(4-Fluorobenzoyl)perhydroazepin-1-yl]propyl}-5-methoxyindole hydrochloride This compound is obtained according to the process described in Example 1 by using, in Stage 3, the 4-(4-fluorobenzoyl)perhydroazepine described in Patent EP 389,352 in place of 3-(4-fluorobenzoylmethyl)pyrrolidine.

Yield: 60%
Melting point: 139°–140° C.

Elemental microanalysis:

|  | C % | H % | N % | Cl % |
|---|---|---|---|---|
| Calculated | 67.48 | 6.80 | 6.30 | 7.97 |
| Found | 67.22 | 6.68 | 6.13 | 7.79 |

EXAMPLE 8

3-{3-[3-(4-Fluorobenzoylmethyl)pyrrolidin-1-yl]propyl}-5-fluoroindole hydrochloride This compound is obtained according to the process described in Example 3 by using, as starting material in Stage 1, 4-fluorophenylhydrazine hydrochloride in place of 4-methoxyphenylhydrazine hydrochloride.

Elemental microanalysis:

|  | C % | H % | N % | Cl % |
|---|---|---|---|---|
| Calculated | 65.95 | 6.02 | 6.69 | 8.46 |
| Found | 65.98 | 6.25 | 6.23 | 8.51 |

EXAMPLE 9

6- Fluoro-3-{1-[3-(5-methoxyindol-3-yl)propyl]pyrrolidin-3-ylmethyl}-1,2-benzisoxazole hydrochloride This compound is obtained according to the process described in Example 3 by replacing, in Stage 3, 3-(4-fluorobenzoylmethyl)pyrrolidine by the 3-[(pyrrolidin-3-yl)methyl]-6-fluoro-1,2-benzisoxazole obtained according to the process described in Patent EP 0,6 10, 134.

Elemental microanalysis:

|  | C % | H % | N % | Cl % |
|---|---|---|---|---|
| Calculated | 64.93 | 6.13 | 9.46 | 7.99 |
| Found | 63.31 | 6.08 | 8.92 | 8.04 |

EXAMPLE 10

3-{2-[3-(4-Fluorobenzoylmethyl)pyrrolidin-1-yl]ethyl}-5-chloro-1H-indazole hydrochloride Stage 1
3-Amino-3-(5-chloro-2-nitrophenyl)propanoic acid A mixture of 50 g of 5-chloro-2-nitrobenzaldehyde (0.27 mol), 4 eq of formic acid (49.6 g) and 1.3 eq of malonic acid (36.6 g) is brought to 40°–45° C. in a three-necked flask equipped with a thermometer, a mechanical stirrer and a reflux condenser surmounted by a drying tube containing silica gel. 2.5 eq of ammonium formate are added. The reaction mixture is heated for 1 hour at 60°–70° C. and then for 5 hours at 90°–95° C. Acidification is then carded out by adding 9.8 eq of 36% hydrochloric acid (110 ml) and 20 ml of water, reflux being continued for one hour. The reaction mixture is concentrated to dryness and the residue is then redissolved in water. The pH is brought to approximately 7.8 with 2M sodium hydroxide. The precipitate obtained is filtered off and then dried in a desiccator. The amino acid is obtained in the form of the internal salt.

Stage 2
(5-Chloro-1H-indazol-3-yl)acetic acid

The amino acid obtained in Stage 1 is dissolved with 3 equivalents of sodium hydroxide pellets in 600 ml of water in a three-necked flask equipped with a thermometer, a mechanical stirrer, a dropping funnel and a reflux condenser surmounted by a bubbler. The mixture is brought to 30°–40° C. and 5.7 g of active charcoal are added. Hydrazine monohydrate is slowly added (2.1 eq, i.e. 22.7 g). The mixture is stirred for 15 minutes at 30°–40° C. and then for 3 hours at 80°–85° C. The reaction mixture is cooled. After filtration, the reaction mixture is acidified with 75 ml of 36% hydrochloric acid. The precipitate formed is filtered off on sintered glass and then dried in a desiccator.
Melting point: 193° C.

Stage 3
2-(5-Chloro-1H-indazol-3-yl)ethanol 6.7 g (0.95 eq) of lithium aluminum hydride are introduced into a three-necked flask equipped with a thermometer, a dropping funnel and a reflux condenser surmounted by a bubbler connected to a drying tube containing silica gel and are covered with 80 ml of tetrahydrofuran. The acid obtained in the preceding stage, dissolved in 420 ml of tetrahydrofuran, is slowly added to the hydride. Reflux is maintained for 24 hours with stirring. The reaction mixture, cooled to room temperature, is hydrolyzed with 180 ml of saturated magnesium sulfate solution (10 eq). A precipitate is formed which is filtered off on celite. The filtrate is concentrated to dryness. The residue is taken up in ethyl acetate with a small amount of water. The organic phase is again filtered, in order to remove the inorganic salts, and the filtrate is concentrated. The product is purified by chromatography on a silica column, using ethyl acetate as eluent.

Stage 4
3-(2-Bromoethyl)-5-chloro-1H-indazole

The expected product is obtained, according to the process described in Stage 2 of Example 1, from the compound obtained in the preceding stage.

Stage 5
3-{2-[3-(4-Fluorobenzoylmethyl)pyrrolidin-1-yl]ethyl}-5-chloro-1H-indazole The expected product is obtained, according to the process described in Stage 3 of Example 1, from the compound described in the preceding stage.

Stage 6
3-{2-[3-(4-Fluorobenzoylmethyl)pyrrolidin-1-yl]ethyl}-5-chloro-1H-indazole hydrochloride The hydrochloride of the product obtained in the preceding stage is obtained according to the process described in Stage 4 of Example 1.

Pharmacological Study of the Compounds of the Invention

The compounds of the invention were tested in comparison with haloperidol, clozapine and a compound, named Ref. A, which has a piperidine ring in place of a pyrrolidine or perhydroazepine ring, as is the case in the compounds of the invention.

Ref. A: 3-{3-[4-(4-Fluorobenzoyl)piperidin-1-yl]propyl}-5-methoxyindole hydrochloride.

EXAMPLE 11

Receptor profile of the compounds of the invention

The interaction of these compounds with various receptors was determined by using conventional binding studies, such as those described by M. J. Millan et at. (J. Pharmacol. Exp. Ther., 268, 337–352, 1994 and Drug News Perspectives, 5, 397–406, 1992). The receptor profile of the compounds of the invention is presented in the Table below. The affinities of the compounds are expressed in Ki.

| Receptor profile (Ki, nM) | | | | | | | |
|---|---|---|---|---|---|---|---|
| Examples | $D_2$ | $5\text{-}HT_{2A}$ | $5\text{-}HT_{2C}$ | $5\text{-}HT_{1A}$ | $D_2/5\text{-}HT_{2A}$ | $D_2/5\text{-}HT_{2C}$ | $D_2/5\text{-}HT_{1A}$ |
| Haloperidol | 1 | 83 | 5754 | 2818 | 0.01 | <0.01 | <0.01 |
| Clozapine | 186 | 23 | 8.7 | 295 | 8.11 | 21 | 0.6 |
| Ref. A | 11 | 8.5 | 98 | 5.6 | 1.3 | 0.1 | 2 |
| Ex. 1 | 110 | 1.6 | 50 | 0.6 | 69 | 22 | 183 |
| Ex. 2 | 132 | 1.3 | 16 | 141 | 101 | 8.3 | 0.9 |
| Ex. 3 | 5.2 | 1.0 | 3.3 | 1.0 | 5.2 | 1.6 | 5.2 |
| Ex. 4 | 6.3 | 1.20 | 4.0 | 1.1 | 5.2 | 1.6 | 5.7 |
| Ex. 5 | 7.1 | 1.7 | 3.8 | 0.4 | 4.2 | 1.9 | 17.8 |
| Ex. 6 | 15.4 | 4.3 | 17 | 39 | 3.6 | 0.9 | 0.4 |
| Ex. 7 | 43.5 | 2.7 | 117 | 0.7 | 1.6 | 0.4 | 62 |
| Ex. 8 | 9.5 | 6.6 | 19.0 | 12.3 | 1.4 | 0.5 | 0.8 |
| Ex. 9 | 98 | 3.2 | 7.9 | 0.7 | 31 | 13 | 143 |

These results show the strong affinity of the compounds of the invention for $5\text{-}HT_{1A}$, $5\text{-}HT_{2A}$ and more particularly $5\text{-}HT_{2C}$ receptors with respect to $D_2$ receptors, after the fashion of clozapine and unlike haloperidol and the compound Ref. A.

EXAMPLE 12

Antipsychotic properties

In order to determine the antipsychotic properties of the compounds of the invention, a well-established test was used in which all antipsychotics are clinically active, as has been shown by A. Y. Deutch et al. (Schizophrenia Research, 4, 121–156, 1991): inhibition of the verticalization induced by a dopaminergic agonist: apomorphine (according to the protocol described by P. Protais et al., Psychopharmacol., 50, 1–6, 1976).

An activity in these tests seems to reflect a blockage of the mesolimbic dopaminergic pathways which are believed to be hyperactive in schizophrenics, as described by P. C. Waldmeier et al. (Eur. J. Pharmacol., 55, 363–373, 1979) and A. Y. Deutch, cited above. The activities of the compounds of the invention were compared with those of haloperidol and clozapine.

Verticalization test with apomorphine in mice

The experiment was performed on male CF (Charles River) mice of average weight 25 g. Thirty minutes before the start of the test, each mouse was placed in a cylindrical cage (Ø 12 cm×14 cm), with vertical metal bars and a smooth plastic lid, after having received a subcutaneous injection of solvent or of product. At $T_0$, a solution of apomorphine (0.75 mg/kg) or of physiological saline was administered subcutaneously to the animal, which is returned to the barred cage. At $T_{10}$ (10 minutes) and at $T_{20}$ (20 minutes), a score was attributed to each animal after observation for approxi-mately one minute:

score 0 (4 paws on the floor)

score 1 (upright animal, front paws on the vertical bars);

score 2 (animal clinging by the 4 paws to the bars).

The total score of the 2 measurements then represents the verticalization value of the animal, which is used for the statistical analysis.

EXAMPLE 13

Catalepsy in rats

In order to determine the potential of the compounds of the invention to generate a syndrome of extrapyramidal type in man, the capacity to induce a catalepsy in rats was examined. This phenomenon is due to an antagonism of the nigrostriatal dopaminergic transmission. The activities of the compounds were compared with those of haloperidol and clozapine.

Protocol

Male Wistar rats (220–240 g) were placed in individual cages and food was withheld the day before the test. The test used to evaluate the cataleptogenic properties of a product consists in placing each hind paw of the animal on the front paw situated on the same side and in measuring the time in seconds during which the animal retained this "crossed paws" position, for up to 30 seconds, as described by P. C. Waldmeier et al. (Eur. J. Pharmacol., 55, 363–373, 1979). Each animal was subjected to three tests, at intervals of one minute; the mean value of the three tests then represents the catalepsy time of the animal, which is used for the statistical analysis.

The product to be tested was administered to the animal subcutaneously 30 minutes before the test.

The results of the induction of catalepsy in rats are presented in the Table below:

The effective cataleptogenic dose $ED_{50}$ is that which induces catalepsy for a mean duration of 15 seconds, that is to say 50% of the maximum duration of the test (30 seconds).

The results of the tests described in Examples 12 and 13 are presented in the Table below:

| Examples | Verticalization (Apomorphine) $ID_{50}$ (mg/kg/S.C.) | Induction of catalepsy $ED_{50}$ (mg/kg/S.C.) | $ED_{50}/ID_{50}$ Ratio |
|---|---|---|---|
| Haloperidol | 0.01 | 0.14 | 14 |
| Clozapine | 2.2 | >40.0 | >18 |
| Ref. A | 0.1 | 1.4 | 14 |
| Ex. 1 | 0.31 | >40.0 | >129 |
| Ex. 2 | 1.25 | >40.0 | >32 |
| Ex. 3 | 0.15 | >40.0 | >266 |
| Ex. 4 | 0.3 | >40.0 | >133 |
| Ex. 5 | 0.13 | >40.0 | >307 |
| Ex. 7 | 0.5 | >40.0 | >80 |
| Ex. 8 | 0.5 | >40.0 | >80 |
| Ex. 9 | 1.0 | >40.0 | >40 |

These results show the strong verticalization-inhibiting antipsychotic activity of the compounds of the invention in the absence of extrapyramidal properties (induction of catalepsy), after the fashion of clozapine and unlike haloperidol and the compound Ref. A.

EXAMPLE 14

Pharmaceutical composition

Preparation formula for 1000 tablets containing a 1 mg dose

Compound of Example 2 1 g
Hydroxypropylcellulose 2 g
Wheat starch 10 g
Lactose 100 g
Magnesium stearate 3 g
Talc 3 g

We claim:

1. A compound selected from the group having formula (I):

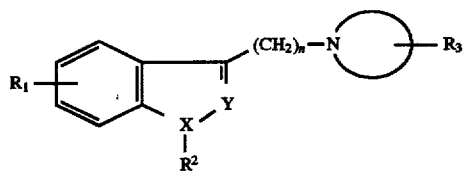

in which:
- $R_1$ represents hydrogen, halogen, linear or branched $(C_1-C_6)$alkyl, linear or branched $(C_1-C_6)$alkoxy, trihalomethyl, or hydroxyl,
- $R_2$ represents hydrogen or linear or branched $(C_1-C_6)$ alkyl or a phenyl group which is unsubstituted or substituted by halogen, alkyl, alkoxy, hydroxyl, or trihalomethyl,

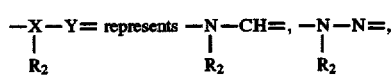

or represents —O—N=,
n is 1, 2, 3, 4, 5, or 6

represents any one of the following groups:

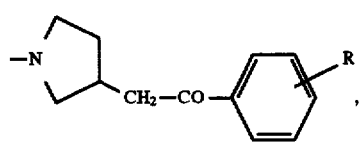

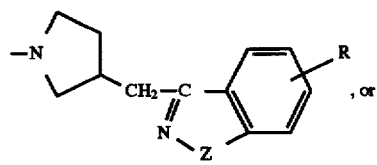

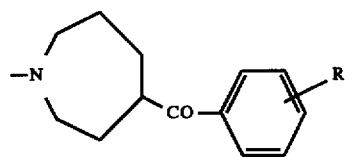

in which:
R represents hydrogen, halogen, linear or branched $(C_1-C_6)$alkyl, linear or branched $(C_1-C_6)$alkoxy, hydroxyl, or trihalomethyl, Z represents oxygen, sulfur, or —NH—, its isomers and its addition salts with a pharmaceutically-acceptable acid or base.

2. A compound of claim 1, wherein

3. A compound of claim 1, wherein n is equal to 2.
4. A compound of claim 1, wherein n is equal to 3.
5. A compound of claim 1, wherein

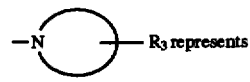

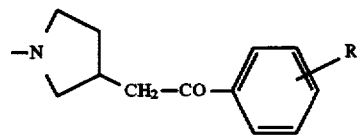

6. A compound of claim 1, wherein

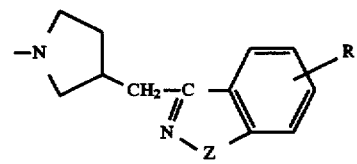

7. A compound of claim 1, wherein

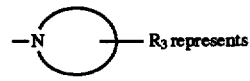

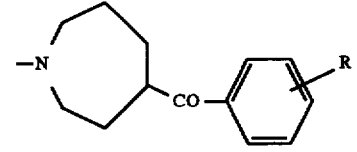

8. A method for treating a living animal body afflicted with a schizophrenic condition comprising the step of administering to the living animal body an amount of a compound of claim 1 which is effective for alleviation of said condition.

9. A pharmaceutical composition useful in treating schizophrenia comprising as active principle an effective amount of a compound of claim 1, together with one or more pharmaceutically-acceptable excipients or vehicles.

* * * * *

UNITED STATES PATENT AND TRADEMARK OFFICE
CERTIFICATE OF CORRECTION

PATENT NO. : 5,703,070
DATED : Dec. 30, 1997
INVENTOR(S) : G. Lavielle, O. Muller, M. Millan, V. Audinot It is certified that error appears in the above-indentified patent and that said Letters Patent is hereby corrected as shown below:

Title Page, [57] ABSTRACT, line 2: In the last line of the formula, "$R^2$" should read -- $R_2$ --.

Column 2, line 26: In the last line of the formula, "$R^2$" should read -- $R_2$ --.

Column 9, line 43: "carded" should read -- carried --.

Column 13, line 16: In the last line of the formula, "$R^2$" should read -- $R_2$ --. Page 19, line 3

Column 13, line 30: Delete the word "represents".

Signed and Sealed this

Seventh Day of April, 1998

Attest:

BRUCE LEHMAN

Attesting Officer

Commissioner of Patents and Trademarks